United States Patent [19]

Brenner

[11] Patent Number: 5,780,231
[45] Date of Patent: Jul. 14, 1998

[54] DNA EXTENSION AND ANALYSIS WITH ROLLING PRIMERS

[75] Inventor: Sydney Brenner, Cambridge, England

[73] Assignee: Lynx Therapeutics, Inc., Hayward, Calif.

[21] Appl. No.: 611,155

[22] Filed: Mar. 5, 1996

Related U.S. Application Data

[63] Continuation-in-part of Ser. No. 560,313, Nov. 17, 1995.
[51] Int. Cl.$^6$ .............. C12Q 1/68; C12P 19/34; C12N 15/00
[52] U.S. Cl. .............. 435/6; 435/91.2; 935/77; 935/78
[58] Field of Search .............. 435/6, 91.1, 91.2

[56] References Cited

U.S. PATENT DOCUMENTS

| | | | |
|---|---|---|---|
| 4,293,652 | 10/1981 | Cohen | 435/6 |
| 4,942,124 | 7/1990 | Church | 435/6 |
| 4,994,370 | 2/1991 | Silver et al. | 435/6 |
| 5,102,785 | 4/1992 | Livak et al. | 435/6 |
| 5,149,625 | 9/1992 | Church | 435/6 |
| 5,310,893 | 5/1994 | Erlich et al. | 536/24.31 |
| 5,405,746 | 4/1995 | Uhlen | 435/6 |
| 5,407,799 | 4/1995 | Studier | 435/6 |
| 5,413,909 | 5/1995 | Bassam et al. | 435/6 |
| 5,427,911 | 6/1995 | Ruano | 435/6 |
| 5,496,699 | 3/1996 | Sorenson | 435/6 |
| 5,508,169 | 4/1996 | Deugau et al. | 435/6 |

FOREIGN PATENT DOCUMENTS

| | | |
|---|---|---|
| 303459 | 2/1989 | European Pat. Off. |
| 649852 | 4/1994 | European Pat. Off. |
| 630972 | 12/1994 | European Pat. Off. |
| PCT/GB94/01675 | 2/1995 | WIPO |
| PCT/US95/03678 | 10/1995 | WIPO |

OTHER PUBLICATIONS

Gramegna et al., Research in Virology 144:307–309 (1993).
Martin, Genome 31:1073–1080 (1989).
McBride et al., Clinical Chemistry 35(11):2196–2201 (1989).
Berg et al., Biotechniques 17(5):896–901 (1994).
Kasai et al., Nucleic Acids Research20(24): 6509–6515 (1992).
Boles et al., Current Genetics 28: 197–198 (1995).
Wu et al., PNAS 86:2757–2760 (1990).
Scharf et al., PNAS 86:6215–6219 (1990).
Okayama et al., J. Laboratory and Clinical Medicine 114(2): 105–113 (1989).
Szybalski, Gene 135: 279–290 (1993).
International Application PCT/GB93/01452 (Publ. No. wo 95/05182) Inventor Sibson Title Process for categorizing nucleotide sequence population Publication Date 20 Jan. 1994.
International Application PCT/GB95/00109 (Publ. No. wo 93/20053) Inventor Sibson Title Sequencing of nucleic acids Publcation Date 27 Jul. 1995.
International Application PCT/US93/01552 (Publ. No. wo 93/17126) Inventor Chetverin and Kramer Title Novel oligonucleotide arrays and their use for sorting, isolating, sequencing, and manipulating nucleic acids Publication Date 2 Sept. 1993.
International Application PCT/US92/01905 (Publ. No. wo 92/15712) Inventor Goelet et al Title Nucleic acid typing by polymerase extension of oligonucleotides using terminator mixtures Publication Date 17 Sept. 1992.
International Application PCT/US94/07086 (Publ. No. wo 94/05182) Inventor Caskey et al Title Parallel primer extension approach to nucleic acid sequence analysis Publication Date 5 Jan. 1995.
European patent Application 90107066.4 Publ. No. 0 392 546 A2 Inventor Drmanac and Crkvenjakov Title Process for determination of a complete or a partial contents of very short sequences in the samples of nucleic acids connected to the discrete particles of microscopic size by hybridization with oligonucleotide probes Publication Date 17 Oct. 1990.

(List continued on next page.)

Primary Examiner—W. Gary Jones
Assistant Examiner—Ethan Whisenant
Attorney, Agent, or Firm—Stephen C. Macevicz

[57] ABSTRACT

A novel "primer walking" method for DNA sequencing is provided that comprises repeated cycles nucleotide identification by selective extension and primer advancement along a template by template mutation. An important feature of the invention is providing a set of primers, referred to herein as "rolling primers" that contain complexity-reducing nucleotides for reducing the number of primers required for annealing to every possible primer binding site on a sequencing template. Another important feature of the invention is the systematic replacement of at least one of the four nucleotides in the target polynucleotide with its cognate complexity-reducing nucleotide or complement thereof. Sequencing is initiated by annealing rolling primers differing only in their terminal nucleotides to a primer binding site of a sequencing template so that only the rolling primer whose terminal nucleotide forms a perfect complement with the template leads to the formation of an extension product. After amplifying the double stranded extension product to form an amplicon, the terminal nucleotide, and hence its complement in the template, is identified by the identity of the amplicon. The primer binding site of the template of the successfully amplified polynucleotide is then mutated by, for example, oligonucleotide-directed mutagenesis so that a subsequent rolling primer may be selected from the set that forms a perfectly matched duplex with the mutated template at a site which is shifted towards the direction of extension by one nucleotide relative to the binding site of the previous rolling primer. The steps of selective extension, amplification and identification are then repeated. In this manner, the primers "roll" along the polynucleotide during the sequencing process, moving a base at a time along the template with each cycle.

4 Claims, 4 Drawing Sheets

OTHER PUBLICATIONS

Roberts and Macelis, "REBASE–restriction enzymes and methylases", Nucleic Acids Research, 21: 3125–3137 (1993).

Hasan et al., "A novel multistep method for generating precise unidirectional deletions using BspMI, a class–IIS restriction enzyme", Gene, 82: 50: 55–62 (1986).

Hasan et al., "An MboII/FokI trimming plasmid allowing consecutive cycles of precise 1–to 12–base–pair deletions in cloned DNA", Gene, 82: 305–311 (1989).

Szybalski et al., "Class–IIS restriction enzymes—a review", Gene, 100: 13–26 (1991).

Kwok et al., "Effects of primer—template mismatches on the polymerase chain reaction: Human immunodeficiency virus type 1 model studies", Nucleic Acids Research, 18;999–1005 (1990).

Huang et al., "Extension of base mispairs by Taq DNA polymerase: implications for single nucleotide discrimination in PCR", Nucleic Acids Research 20 :4567–4573 (1992).

Short Technical Reports, "Priming Efficiency", BioTechniques, 18: 84–89 (1995).

Martin and Castro, "Base pairing involving deoxyinosine: implications for probe design", Nucleic Acids Research, 13: 8927–8938 (1985).

Kawase et al., "Studies on nucleic acid interactions I. Stabilities of mini–duplexes (dG$_2$A$_4$XA$_4$·dC$_2$T$_4$YT$_4$C$_2$) and self–complementary d(GGGAAXYTTCCC) containing deoxyinosine and other mismatched bases", Nucleic Acids Research, 14: 7727–7736 (1986).

Case–Green and Southern, "Studies on the base pairing properties of deoxyinosine by solid phase hybridization to oligonucleotides", Nucleic Acids Research, 22: 131–136 (1994).

Ausubel et al., "Mutagenesis of Cloned DNA", Current Protocols in Molecular Biology, Chapter 8, John Wiley & Sons, 1995.

Mormeneo ey al., "Precise nucleotide sequence modifications with bidirectionally cleaving class–IIS excision linkers", Gene, 61: 21–30 (1987).

Unrau and Deugau, "Non–Cloning amplification of specific DNA fragments from whole genomic DNA digests using DNA 'indexers'", Gene, 145: 163–169 (1994).

Kato, "Description of the entire mRNA population by a 3'end cDNA fragment generated by a 3'end cDNA fragment generated by class IIS restriction enzymes", Nucleic Acids Research, 23: 3685–3690 (1995).

Zoller et al., "Oligonucleotide–Directed mutagenesis of DNA Fragments Cloned into M13 Vectors", Recombinant DNA Methodology, Chapter 30, Academic Press, Inc., 1989.

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

GGAAGAGGAA GAGGAAGANN NN                      2 2

( 2 ) INFORMATION FOR SEQ ID NO: 2:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GAAGAGGAAG AGGAAGAGNN NN     22

( 2 ) INFORMATION FOR SEQ ID NO: 3:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AAGAGGAAGA GGAAGAGGNN NN     22

( 2 ) INFORMATION FOR SEQ ID NO: 4:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

AGAGGAAGAG GAAGAGGANN NN     22

( 2 ) INFORMATION FOR SEQ ID NO: 5:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GAGGAAGAGG AAGAGGAANN NN     2

( 2 ) INFORMATION FOR SEQ ID NO: 6:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

AGGAAGAGGA AGAGGAAGNN NN     22

( 2 ) INFORMATION FOR SEQ ID NO: 7:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CCTTCTCCTT CTCCTTCTTC CNNNN     25

( 2 ) INFORMATION FOR SEQ ID NO: 8:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 8:

AGTGGCTGGG CATCGGACCG     20

( 2 ) INFORMATION FOR SEQ ID NO: 9:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 9:

GGGGCCCAGT CAGCGTCGAT　　　　　　　　　　　　　　　　　　　　　　　　　　　20

( 2 ) INFORMATION FOR SEQ ID NO: 10:

( i ) SEQUENCE CHARACTERISTICS:
        ( A ) LENGTH: 70 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 10:

AAAAGGAGGA GGCCTTGATA GAGAGGACCT GTTTAAACGT TTAAACGGAT　　　　50

CCTCTTCCTC TTCCTCTTCC　　　　　　　　　　　　　　　　　　　　　　　　　　　70

( 2 ) INFORMATION FOR SEQ ID NO: 11:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 11:

NNNNNNNNAA AAGGAGGAGG CCTTGA　　　　　　　　　　　　　　　　　　　　26

( 2 ) INFORMATION FOR SEQ ID NO: 12:

( i ) SEQUENCE CHARACTERISTICS:
        ( A ) LENGTH: 43 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 12:

NNNNNNNNAG AGAGAGAGAG GAGAGAGAGA GTAGAGAGGA CCG　　　　　　　43

( 2 ) INFORMATION FOR SEQ ID NO: 13:

( i ) SEQUENCE CHARACTERISTICS:
        ( A ) LENGTH: 12 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 13:

AUCUCUCCUG GC　　　　　　　　　　　　　　　　　　　　　　　　　　　　　　　12

DNA EXTENSION AND ANALYSIS WITH ROLLING PRIMERS

This is a continuation-in-part application of co-pending U.S. patent application Ser. No. 08/560,313 filed 17 Nov. 1995.

FIELD OF THE INVENTION

The invention relates generally to a method of DNA sequencing and analysis, and more particularly, to a method of base-by-base sequencing by successive extensions of an oligonucleotide primer.

BACKGROUND

Large-scale sequencing projects typically involve the generation of libraries of progressively smaller clones of portions of the polynucleotide whose sequence is to be determined. Genomic DNA is fragmented and inserted into yeast artificial chromosomes (YACs) or cosmids whose inserts, in turn, are fragmented and inserted into phage or plasmid vectors for sequencing, e.g. Hunkapiller et al, Science, 254: 59–67 (1991). Although large-scale sequencing projects can be carried out by either so-called "directed" or "random" strategies, both approaches involve at least one or two labor intensive steps where templates are prepared for sequencing by one or another variant of the Sanger chain-termination method.

Many proposals have been made for reducing or eliminating these labor intensive steps. For example, one directed strategy involves an initial round of sequencing with a vector-specific "universal" primer followed by repetitive cycles of synthesis of a new sequencing primer generated from the just-acquired sequence information and subsequent new sequence determination with the new primer. In such a manner, one may "walk" along a relatively large sequencing template with a succession of newly determined primers without the need to fragment and subclone the template. A drawback of such an approach is the difficulty of acquiring the new primer at each cycle for making the next round of extensions. Either the process is rendered intolerably slow while one waits for the next primer to be synthesized, or the process is rendered impractical by the need to maintain a library of primers of every possible sequence which, for example, could be more than $1\times10^9$ for a primer 15 nucleotides in length. A proposal to mitigate this difficulty has been made that calls for primers that are assembled from a library of shorter oligonucleotides, such as pentamers or hexamers, e.g., Kotler et al, Proc. Natl. Acad. Sci., 90: 4241–4245 (1993); Kieleczawa et al, Science, 258: 1787–1791 (1992); and the like. But even with hexamers, a library of at least 4096 oligonucleotides is required.

Besides the problem of template preparation, as mentioned above, both directed and random approaches employ the Sanger chain-termination method of sequencing which requires the generation of sets of labeled DNA fragments, each fragment having a common origin and terminating with a known base. The sets of fragments are typically separated by high resolution gel electrophoresis, which must have the capacity of distinguishing very large fragments differing in size by no more than a single nucleotide. Unfortunately, several significant technical problems have seriously impeded efficient scale-up of Sanger-based approaches, either for accommodating longer sequences or for accommodating high-volume sequencing absent massive capital and labor investment. Such problems include i) the gel electrophoretic separation step which is labor intensive, is difficult to automate, and introduces an extra degree of variability in the analysis of data, e.g. band broadening due to temperature effects, compressions due to secondary structure in the DNA sequencing fragments, inhomogeneities in the separation gel, and the like; ii) nucleic acid polymerases whose properties, such as processivity, fidelity, rate of polymerization, rate of incorporation of chain terminators, and the like, are often sequence dependent; iii) detection and analysis of DNA sequencing fragments which are typically present in fmol quantities in spatially overlapping bands in a gel; iv) lower signals because the labeling moiety is distributed over the many hundred spatially separated bands rather than being concentrated in a single homogeneous phase, and v) in the case of single-lane fluorescence detection, the availability of dyes with suitable emission and absorption properties, quantum yield, and spectral resolvability, e.g. Trainor, Anal. Biochem., 62: 418–426 (1990); Connell et al, Biotechniques, 5: 342–348 (1987); Karger et al, Nucleic Acids Research, 19: 4955–4962 (1991); Fung et al, U.S. Pat. No. 4,855,225; and Nishikawa et al, Electrophoresis, 12: 623–631 (1991).

An important advance in sequencing technology could be made if an alternative approach was available for sequencing DNA (i) that did not require high resolution electrophoretic separations of DNA fragments, (ii) that reduced the number of templates required in large-scale sequencing projects, and (iii) that was amenable to simultaneous, or parallel, application to multiple target polynucleotides.

SUMMARY OF THE INVENTION

An object of my invention is to provide a new method and approach for determining the sequence of polynucleotides.

Another object of my invention is to provide a new "primer walking" approach to sequencing that requires fewer primers for implementation.

Still another object of my invention is to provide a method and kits for reducing the number of templates required in large-scale sequencing projects.

Another object of my invention is to provide a method for rapidly analyzing patterns of gene expression in normal and diseased tissues and cells.

A further object of my invention is to provide a method, kits, and apparatus for simultaneously analyzing and/or sequencing a population of many thousands of different polynucleotides, such as a sample of polynucleotides from a cDNA library or a sample of fragments from a segment of genomic DNA.

Still another object of my invention is to provide a method, kits, and apparatus for identifying populations of polynucleotides.

Another object of my invention is to provide a method for sequencing segments of DNA in a size range corresponding to typical cosmid or YAC inserts.

The method of my invention achieves these and other objectives by repeated cycles nucleotide identification by selective extension and primer advancement along a template by template mutation. An important feature of the invention is providing a set of primers, referred to herein as "rolling primers" that contain complexity-reducing nucleotides for reducing the number of primers required for annealing to every possible primer binding site on a sequencing template. Another important feature of the invention is the systematic replacement of at least one of the four nucleotides in the target polynucleotide with its cognate complexity-reducing nucleotide or complement thereof.

Sequencing is initiated by annealing rolling primers differing only in their terminal nucleotides to a primer binding site of a sequencing template so that only the rolling primer whose terminal nucleotide forms a perfect complement with the template leads to the formation of an extension product. After amplifying the double stranded extension product to form an amplicon, the terminal nucleotide, and hence its complement in the template, is identified by the identity of the amplicon. For example, in a simple embodiment, a terminal nucleotide may be identified by the presence or absence of amplicon in four vessels that are used for separate extension and amplification reactions. The primer binding site of the template of the successfully amplified polynucleotide is then mutated by, for example, oligonucleotide-directed mutagenesis so that a subsequent rolling primer may be selected from the set that forms a perfectly matched duplex with the mutated template at a site which is shifted towards the direction of extension by one nucleotide relative to the binding site of the previous rolling primer. The steps of selective extension, amplification and identification are then repeated. In this manner, the primers "roll" along the polynucleotide during the sequencing process, moving a base at a time along the template with each cycle.

Generally, this aspect of my invention is carried out with the following steps: (a) providing a set of primers, i.e. the rolling primers, each primer of the set having an extension region comprising one or more complexity-reducing nucleotides and a terminal nucleotide; (b) forming a template comprising a primer binding site and the polynucleotide whose sequence is to be determined, the primer binding site being complementary to the extension region of at least one primer of the set; (c) annealing a primer from the set to the primer binding site, the extension region of the primer forming a perfectly matched duplex with the template and extending the primer to form a double stranded DNA; (d) amplifying the double stranded DNA to form an amplicon; (e) identifying the terminal nucleotide of the extension region of the primer by the identity of the amplicon; (f) mutating the primer binding site of the template so that the primer binding site is shifted one or more nucleotides in the direction of extension, thereby effectively shortening the target polynucleotide by one or more nucleotides; and (g) repeating steps (c) through (f) until the nucleotide sequence of the polynucleotide is determined.

An important feature of my invention is the capability of applying the method to many different polynucleotides in parallel by the use of oligonucleotide tags. In accordance with this aspect of my invention, each polynucleotide of a population is conjugated with an oligonucleotide tag for transferring sequence information to a tag complement on a spatially addressable array of such complements. That is, a unique tag is attached to each polynucleotide of a population which can be copied and used to shuttle sequence information to its complement at a fixed position on an array of such complements. After a tag hybridizes with its complement, a signal is generated that is indicative of the transferred sequence information. Sequences of the tagged polynucleotides are determined by repeated cycles of information transfer and signal detection at the positions of the corresponding tag complements.

At least two major advantages are gained by using tags to shuttle information to discrete spatial locations rather than sorting an entire population of target polynucleotides to such locations: First, tags are much smaller molecular entities so that the kinetics of diffusion and hybridization are much more favorable. Second, tag loading at the spatially discrete locations only need be sufficient for detection, while target polynucleotide loading would need to be sufficient for both biochemical processing and detection; thus, far less tag needs to be loaded on the spatially discrete sites.

An important feature of this embodiment of my invention is the attachment of an oligonucleotide tag to each polynucleotide of a population such that substantially all different polynucleotides have different tags. As explained more fully below, this is achieved by talking a sample of a full ensemble of tag-polynucleotide conjugates wherein each tag has an equal probability of being attached to any polynucleotide.

Oligonucleotide tags employed in the invention are capable of hybridizing to complementary oligomeric compounds consisting of subunits having enhanced binding strength and specificity as compared to natural oligonucleotides. Such complementary oligomeric compounds are referred to herein as "tag complements." Subunits of tag complements may consist of monomers of non-natural nucleotide analogs or they may comprise oligomers having lengths in the range of 3 to 6 nucleotides or analogs thereof, the oligomers being selected from a minimally cross-hybridizing set. In such a set, a duplex made up of an oligomer of the set and the complement of any other oligomer of the set contains at least two mismatches. In other words, an oligomer of a minimally cross-hybridizing set at best forms a duplex having at least two mismatches with the complement of any other oligomer of the same set. The number of oligonucleotide tags available in a particular embodiment depends on the number of subunits per tag and on the length of the subunit, when the subunit is an oligomer from a minimally cross-hybridizing set. In the latter case, the number is generally much less than the number of all possible sequences the length of the tag, which for a tag n nucleotides long would be $4^n$. Preferred monomers for tag complements include peptide nucleic acid monomers and nucleoside phosphoramidates having a 3'-NHP($=$O)(O$^-$)O—5' linkage with its adjacent nucleoside. The latter compounds are referred to herein as N3'→P5' phosphoramidates. Preferably, both the oligonucleotide tags and their tag complements comprise a plurality of subunits selected from a minimally cross-hybridizing set consisting of natural oligonucleotides of 3 to 6 nucleotides in length.

Generally, this embodiment of my invention is carried out by the following steps: (a) attaching an oligonucleotide tag from a repertoire of tags to each polynucleotide of a population to form tag-polynucleotide conjugates such that substantially all different polynucleotides have different oligonucleotide tags attached; (b) labeling each tag according to the identity of the terminal nucleotides of the respective polynucleotides selectively amplified with a rolling primer; (c) cleaving the tags from the tag-polynucleotide conjugates; and (d) sorting the labeled tags onto a spatially addressable array of tag complements for detection. Preferably, the process is repeated a sufficient number of times to uniquely identify each polynucleotide being sequenced, or to reconstruct a larger polynucleotide from randomly generated fragments.

In summary, my invention provides a novel "primer walking" method for DNA sequencing. Moreover, my invention is readily automated for parallel application and is particularly useful in operations requiring the generation of massive amounts of sequence information, such as large-scale sequencing of genomic DNA fragments, mRNA and/or cDNA fingerprinting, and highly resolved measurements of gene expression patterns.

DEFINITIONS

Figure 1:
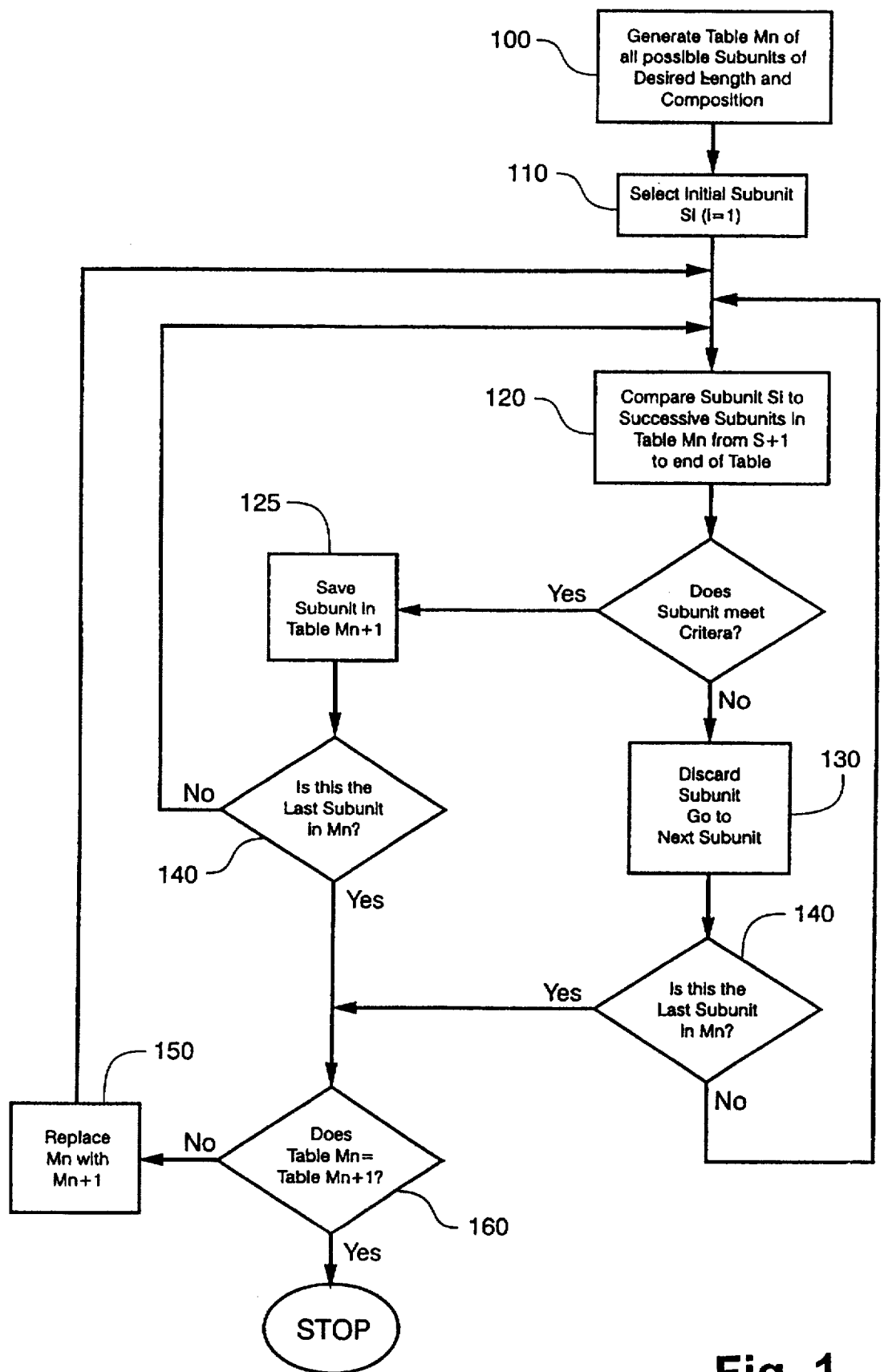
FIG. 1 is a flow chart illustrating a general algorithm for generating minimally cross-hybridizing sets.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, -anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" and "nucleotide" include the natural nucleosides and nucleotides, including 2'-deoxy and 2'-hydroxyl forms, e.g. as described in Kornberg and Baker, DNA Replication, 2nd Ed. (Freeman, San Francisco, 1992). "Natural nucleotide" as used herein refers to the four common natural deoxynucleotides A, C, G, and T. "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity of probes, increase specificity, and the like.

As used herein, "amplicon" means the product of an amplification reaction. That is, it is a population of identical polynucleotides, usually double stranded, that are replicated from a few starting sequences. Preferably, amplicons are produced in a polymerase chain reaction (PCR).

As used herein, "complexity-reducing nucleotide" refers to a natural or non-natural nucleotide (i) that, when paired with either of more than one natural nucleotides, can form a duplex of substantially equivalent stability to that of the same duplex containing cognate natural nucleotide—i.e. the natural nucleotide it replaces, and (ii) that can be processed by enzymes substantially the same as its cognate natural nucleotide. Preferably, complexity-reducing nucleotides do not display degeneracy or ambiguity when processed by DNA polymerases. That is, when a complexity-reducing nucleotide is in a template that is being copied by a polymerase, the polymerase incorporates a unique nucleotide at the site of a complexity-reducing nucleotide. Likewise, when a complexity-reducing nucleotide triphosphate is a substrate for a DNA polymerase, it is incorporated only at the site of a single kind of nucleotide, i.e. one or another of its complements, but not both. Candidate complexity-reducing nucleotides are readily tested in straight forward hybridization assays, e.g. with melting temperature comparisons, and in incorporation assays in which test polymerizations are checked by conventional sequencing or by incorporation of radio-labeled complexity-reducing nucleotides, e.g. Bessman et al, Proc. Natl. Acad. Sci., 44: 633 (1958). Preferably, "substantially equivalent stability," as used herein means that the melting temperature of a test 13-mer duplex, as described in Kawase et al, Nucleic Acids Research, 14: 7727–7736 (1986), is within twenty percent of that of the same duplex containing a natural cognate nucleotide.

DETAILED DESCRIPTION OF THE INVENTION

The invention provides a "primer walking" approach to DNA sequencing in which a special set of primers are used for template copying and mutation. The number of different primers in the set is minimized by a combined use of primers with complexity-reducing nucleotides and the process of template mutation. Within each cycle of copying and mutation, a nucleotide of the polynucleotide is identified and the sequencing template is shortened by one. The shortening of the template results from the mutation that, in effect, converts a nucleotide of target sequence to a nucleotide of primer binding site.

In an important aspect, the invention provides a method of sequencing large numbers of polynucleotides in parallel by using oligonucleotide tags to shuttle sequence information obtained in "bulk" or solution phase biochemical processes to discrete spatially addressable sites on a solid phase. Signals generated at the spatially addressable sites convey the sequence information carried by the oligonucleotide tag. As explained more fully below, sequencing is preferably carried out by alternating cycles of identifying nucleotides and shortening the target polynucleotides by use of rolling primers.

In one aspect, the oligonucleotide tags of the invention comprise a plurality of "words" or subunits selected from minimally cross-hybridizing sets of subunits. Subunits of such sets cannot form a duplex or triplex with the complement of another subunit of the same set with less than two mismatched nucleotides. Thus, the sequences of any two oligonucleotide tags of a repertoire that form duplexes will never be "closer" than differing by two nucleotides. In particular embodiments, sequences of any two oligonucleotide tags of a repertoire can be even "further" apart, e.g. by designing a minimally cross-hybridizing set such that subunits cannot form a duplex with the complement of another subunit of the same set with less than three mismatched nucleotides, and so on. Usually, oligonucleotide tags of the invention and their complements are oligomers of the natural nucleotides so that they may be conveniently processed by enzymes, such as ligases, polymerases, nucleases, terminal transferases, and the like.

In another aspect of the invention, tag complements consist of non-natural nucleotide monomers which encompass a range of compounds typically developed for antisense therapeutics that have enhanced binding strength and enhanced specificity for polynucleotide targets. As mentioned above under the definition of "oligonucleotide," the compounds may include a variety of different modifications of the natural nucleotides, e.g. modification of base moieties, sugar moieties, and/or monomer-to-monomer linkages. Such compounds also include oligonucleotide loops, oligonucleotide "clamps," and like structures that promote enhanced binding and specificity.

Rolling Primers

Preferably, rolling primers are from 15 to 30 nucleotide in length and have the following form:

$$X_1X_2 \ldots X_kYY \ldots YN$$

where the $X_i$'s are nucleotides, preferably arranged in repetitive subunits; Y's are complexity-reducing nucleotides or their complements; and N is a terminal nucleotide of either A, C, G, or T, or a complexity-reducing nucleotide, such as deoxyinosine. The segments of $X_i$ nucleotides, referred to herein as the "template positioning segments," are preferably arranged in repetitive subunits so that the primer is properly registered on the primer binding site with the terminal nucleotide juxtaposed with the first nucleotide of target polynucleotide. Preferably, the repeat subunit is long enough so that if the primer is out of register by one or more repeat subunits, it will be too unstable to remain annealed to the template. Preferably, the repeat subunit is from 4 to 8 nucleotides in length. As will become more apparent below, arranging the template positioning segment as a series of identical subunits reduces the overall number of primers required in a set of rolling primers. Preferably, the template positioning segments are selected from a group of no more than two nucleotides, at least one of which is a complement of a complexity-reducing nucleotide being employed. In preferred embodiments, the underlined $X_k$ indicates the position at which the template is mutated by way of oligonucleotide-directed mutagenesis, e.g. a technique fully described in Current Protocols in Molecular Biology (John Wiley & Sons, New York, 1995).

The segment YY . . . YN is referred to herein as the "extension region" of the primer, as the primer is extended from this end along the template. Preferably, extension is carried out by a polymerase so that YY . . . YN is in a 5'→3' orientation. However, the orientation could be 3'→5' with other methods of extension, e.g. by ligating oligonucleotide blocks as described U.S. Pat. No. 5,114,839. An important feature of the invention is that extension only take place when the terminal nucleotide, N, forms a Watson-Crick base pair with the adjacent nucleotide in the template. The extension region comprises the minimal number of nucleotides greater than two that can form a stable duplex with the template, even if there is a mismatch at the $X_k$ position. That is, in the preferred embodiments, the duplex between the extension region and the template must be stable enough to carry out the oligonucleotide-directed mutagenesis. Preferably, the extension region comprises from 3 to 6 nucleotides, and most preferably, it comprises 4 nucleotides.

Preferably, Y is selected from the group consisting of deoxyadenosine (A) and deoxyinosine (I).

The number of rolling primers required for a particular embodiment depends on several factors, including the type of complexity-reducing nucleotides employed, the length of the primer, the length of the extension region, and the repeat subunit length of the template positioning segment. For example, the following set of primers (SEQ ID NO:1 through SEQ ID NO:6) has a template positioning segment 18 nucleotides in length made up of subunits of G's and A's 6 nucleotides in length.

| Subgroup | Rolling Primer Sequence |
| --- | --- |
| (1) | GGAAGAGGAAGAGGAAGAYYYN |
| (2) | GAAGAGGAAGAGGAAGAGYYYN |
| (3) | AAGAGGAAGAGGAAGAGGYYYN |
| (4) | AGAGGAAGAGGAAGAGGAYYYN |
| (5) | GAGGAAGAGGAAGAGGAAYYYN |
| (6) | AGGAAGAGGAAGAGGAAGYYYN |

If Y is A or I and N is A, C, I, or T, then the above set of rolling primers includes 192 (=6×2³×4) primers. In particular, each "YYY" represents all of the following sequences: AAA, AAI, AII, AIA, IAI, IAA, IIA, and III. As can be seen from the above example, a template positioning segment is available for shifting the primer one nucleotide in the direction of extension after any cycle. That is, if a primer from subgroup (5) were employed in a cycle, the next primer employed would be selected from subgroup (6), if a primer from subgroup (6) were employed in a cycle, the next primer employed would be selected from subgroup (1), and so on. When PCR is used to copy and amplify the template, the template is, in effect, shortened by one nucleotide in each cycle.

Alternatively, the binding strength of the extension region can be improved by substituting G for I and diaminopurine (D) for A in all positions, except those immediately adjacent to the terminal nucleotide. That is, an alternative set of "YYY" sequences include DDA, DDI, DGI, DGA, GDI, GDA, GGI, and GGA.

Sequencing with Rolling Primers

Prior to sequencing, a target polynucleotide is treated so that one or more kinds of nucleotide are substituted with their cognate complexity-reducing nucleotides. In a preferred embodiment, this is conveniently accomplished by replicating the target polynucleotide in a PCR wherein dGTP is replaced with dITP. A template for sequencing is then prepared by joining the target polynucleotide to a primer binding site. Typically, this is accomplished by inserting the target polynucleotide into a vector which carries the primer binding site. Preferably, the primer binding site is in the 3' direction relative to the target polynucleotide so that primer extensions can be carried out with a DNA polymerase. Such insertion is conveniently carried out using a blunt-end-cutting restriction endonuclease, such as Stu I or Ecl 136 II, if the rolling primers described above are employed. These enzymes leave a three-base sequence adjacent to the beginning of the target polynucleotide that is complementary to the primers described above. Preferably, a primer, referred herein as the "T" primer, is located at the other end of the target polynucleotide so that it can be amplified by PCR. For example, sequencing can be initiated on such a template (SEQ ID NO:7) in four separate reactions as shown below, assuming the use of the primers described above.

| Reaction 1 | GGAAGAGGAAGAGGAAGAAI I A-> | | |
| --- | --- | --- | --- |
| | ...CCTTCTCCTTCTCCTTCTTCCNNNN | ...NNNBBBB | ...BB ... |
| Reaction 2 | GGAAGAGGAAGAGGAAGAAI I C-> | | |
| | ...CCTTCTCCTTCTCCTTCTTCCNNNN | ...NNNBBBB | ...BB ... |
| Reaction 3 | GGAAGAGGAAGAGGAAGAAI I I -> | | |
| | ...CCTTCTCCTTCTCCTTCTTCCNNNN | ...NNNBBBB | ...BB ... |
| Reaction 4 | GGAAGAGGAAGAGGAAGAAI I T-> | | |
| | ...CCTTCTCCTTCTCCTTCTTCCNNNN | ...NNNBBBB | ...BB ... | where "NNNN ... NNN" represents the target polynucleotide and "BBBB ... BB" represents the complement of a T primer binding site for amplifying the sequences by PCR. The underlined sequences indicate the extension regions of the rolling primers. The template positioning segment of the primers was arbitrarily chosen to correspond to a primer from subgroup (1) described above. If it is assumed—to illustrate the method—that the sequence of the polynucleotide adjacent to the rolling primer binding site is "TAIC," then only Reaction 1 will result in the formation of an amplicon, and the first nucleotide of the polynucleotide is identified as T. Preferably, prior to amplification, the primer is extended with a high fidelity DNA polymerase, such as Sequenase, in the presence of dATP, dCTP, dITP, and dTTP in the preferred embodiments. It should be understood that selective extension may also be carried out in a single vessel, for example, if labeled primers are employed and the extension products are separated from the primers that fail to extend. The important feature is that only primers whose terminal nucleotide forms a correct Watson-Crick basepair with the template are extended. Preferably, after extension, any single stranded DNA in the reaction mixture is digested with a single stranded nuclease, such as Mung bean nuclease. After such extension and digestion, the remaining double stranded DNA is then amplified, again in the presence of dATP, dCTP, dITP, and dTTP in the preferred embodiments, to produce an amplicon. Preferably, this amplification is accomplished by 5–10 cycles of PCR so that there is little or no likelihood of anomalous amplification products being produced.

Samples of the amplicon from Reaction 1 are removed and aliquotted into four new vessels containing following primers from subgroup (2):

Since the first nucleotide of the target polynucleotide was determined in the previous cycle, one selects primers from subgroup (2) whose extension regions have the form "IIAN," as shown. This creates a mismatch at the underlined T in the lower strands, which is mutated to C in any amplicon produced by oligonucleotide-directed mutagenesis. That is, the primer is the oligonucleotide directing the mutation of the site in the amplicon. Thus, the "T" is converted into a "C" in the amplicons. Since the second nucleotide of the target is A, both Reactions 7 and 8 lead to the production of amplicons. Either amplicon may be sampled for the next cycle since only a single target polynucleotide is presently being considered. As explained more fully below, an additional "pooling" step must be carried out when multiple polynucleotides are simultaneously sequenced.

As before, samples of one of the two amplicons are distributed into four new vessels containing primers from subgroup (3) with an extension region having the form "IAIN".

| Reaction 9 | AAGAGGAAGAGGAAGAGGI AI A-> | | |
| --- | --- | --- | --- |
| | ...CCTTCTCCTTCTCCTTCTCCCTANN | ...NNNBBBB | ...BB |
| Reaction 10 | AAGAGGAAGAGGAAGAGGI AI C-> | | |
| | ...CCTTCTCCTTCTCCTTCTCCCTANN | ...NNNBBBB | ...BB |
| Reaction 11 | AAGAGGAAGAGGAAGAGGI AI I -> | | |
| | ...CCTTCTCCTTCTCCTTCTCCCTANN | ...NNNBBBB | ...BB |
| Reaction 12 | AAGAGGAAGAGGAAGAGGI AI T-> | | |
| | ...CCTTCTCCTTCTCCTTCTCCCTANN | ...NNNBBBB | ...BB |

Both Reactions 9 and 10 will produce amplicons; thus, the third base is identified as an "I." For the next cycle, this then leads to the selection of primers from subgroup (4) having an extension region with the form "AIAN," and the process is continued.

Constructing Oligonucleotide Tags from Minimally Cross-Hybridizing Sets of Subunits The nucleotide sequences of the subunits for any minimally cross-hybridizing set are conveniently enumerated by simple computer programs following the general algorithm illustrated in FIG. 1, and as exemplified by program minhx whose source code is listed in Appendix I. Minhx computes all minimally cross-hybridizing sets having subunits composed of three kinds of nucleotides and having length of four.

| Reaction 5 | GAAGAGGAAGAGGAAGAGI I AA-> | | |
| --- | --- | --- | --- |
| | ...CCTTCTCCTTCTCCTTCTTCCTNNN | ...NNNBBBB | ...BB |
| Reaction 6 | GAAGAGGAAGAGGAAGAGI I AC-> | | |
| | ...CCTTCTCCTTCTCCTTCTTCCTNNN | ...NNNBBBB | ...BB |
| Reaction 7 | GAAGAGGAAGAGGAAGAGI I AI-> | | |
| | ...CCTTCTCCTTCTCCTTCTTCCTNNN | ...NNNBBBB | ...BB |
| Reaction 8 | GAAGAGGAAGAGGAAGAGI I AT-> | | |
| | ...CCTTCTCCTTCTCCTTCTTCCTNNN | ...NNNBBBB | ...BB |

The algorithm of FIG. 1 is implemented by first defining the characteristic of the subunits of the minimally cross-hybridizing set, i.e. length, number of base differences between members, and composition, e.g. do they consist of two, three, or four kinds of bases. A table $M_n$, n=1, is generated (100) that consists of all possible sequences of a given length and composition. An initial subunit $S_1$ is selected and compared (120) with successive subunits $S_i$ for i=n+1 to the end of the table. Whenever a successive subunit has the required number of mismatches to be a member of the minimally cross-hybridizing set, it is saved in a new table $M_{n+1}$ (125), that also contains subunits previously selected in prior passes through step 120. For example, in the first set of comparisons, $M_2$ will contain $S_1$; in the second set of comparisons, $M_3$ will contain $S_1$ and $S_2$; in the third set of comparisons, $M_4$ will contain $S_1$, $S_2$, and $S_3$; and so on. Similarly, comparisons in table $M_j$ will be between $S_j$ and all successive subunits in $M_j$. Note that each successive table $M_{n+1}$ is smaller than its predecessors as subunits are eliminated in successive passes through step 130. After every subunit of table $M_n$ has been compared (140) the old table is replaced by the new table $M_{n+1}$, and the next round of comparisons are begun. The process stops (160) when a table $M_n$ is reached that contains no successive subunits to compare to the selected subunit $S_i$, i.e. $M_n = M_{n+1}$.

As mentioned above, preferred minimally cross-hybridizing sets comprise subunits that make approximately equivalent contributions to duplex stability as every other subunit in the set. Guidance for selecting such sets is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Biol., 26: 227–259 (1991);and the like. For shorter tags, e.g. about 30 nucleotides or less, the algorithm described by Rychlik and Wetmur is preferred, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed.

A preferred embodiment of minimally cross-hybridizing sets are those whose subunits are made up of three of the four natural nucleotides. As will be discussed more fully below, the absence of one type of nucleotide in the oligonucleotide tags permits target polynucleotides to be loaded onto solid phase supports by use of the 5'→3' exonuclease activity of a DNA polymerase. The following is an exemplary minimally cross-hybridizing set of subunits each comprising four nucleotides selected from the group consisting of A, G, and T:

TABLE I

| Word: | $w_1$ | $w_2$ | $w_3$ | $w_4$ |
|---|---|---|---|---|
| Sequence: | GATT | TGAT | TAGA | TTTG |
| Word: | $w_5$ | $w_6$ | $w_7$ | $w_8$ |
| Sequence: | GTAA | AGTA | ATGT | AAAG |

In this set, each member would form a duplex having three mismatched bases with the complement of every other member.

Further exemplary minimally cross-hybridizing sets are listed below in Table I. Clearly, additional sets can be generated by substituting different groups of nucleotides, or by using subsets of known minimally cross-hybridizing sets.

TABLE II

Exemplary Minimally Cross-Hybridizing Sets of 4-mer Subunits

| Set 1 | Set 2 | Set 3 | Set 4 | Set 5 | Set 6 |
|---|---|---|---|---|---|
| CATT | ACCC | AAAC | AAAG | AACA | AACG |
| CTAA | AGGG | ACCA | ACCA | ACAC | ACAA |
| TCAT | CACG | AGGG | AGGC | AGGG | AGGC |
| ACTA | CCGA | CACG | CACC | CAAG | CAAC |
| TACA | CGAC | CCGC | CCGG | CCGC | CCGG |
| TTTC | GAGC | CGAA | CGAA | CGCA | CGCA |
| ATCT | GCAG | GAGA | GAGA | GAGA | GAGA |
| AAAC | GGCA | GCAG | GCAC | GCCG | GCCC |
|  | AAAA | GGCC | GGCG | GGAC | GGAG |

| Set 7 | Set 8 | Set 9 | Set 10 | Set 11 | Set 12 |
|---|---|---|---|---|---|
| AAGA | AAGC | AAGG | ACAG | ACCG | ACGA |
| ACAC | ACAA | ACAA | AACA | AAAA | AAAC |
| AGCG | AGCG | AGCC | AGGC | AGGC | AGCG |
| CAAG | CAAG | CAAC | CAAC | CACC | CACA |
| CCCA | CCCC | CCCG | CCGA | CCGA | CCAG |
| CGGC | CGGA | CGGA | CGCG | CGAG | CGGC |
| GACC | GACA | GACA | GAGG | GAGG | GAGG |
| GCGG | GCGG | GCGC | GCCC | GCAC | GCCC |
| GGAA | GGAC | GGAG | GGAA | GGCA | GGAA |

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are capable of specific hybridization. As mentioned above, N3'→P5' oligonucleotide phosphoramidates are preferred materials for tag complements in some embodiments. Synthesis of such compounds is described in Chen et al, Nucleic Acids Research, 23: 2661–2668 (1995) and in Internation application PCT/US95/03575. In some embodiments, tags may comprise naturally occuring nucleotides that permit processing or manipulation by enzymes, while the corresponding tag complements may comprise non-natural nucleotide analogs, such as peptide nucleic acids, or like compounds, that promote the formation of more stable duplexes during sorting.

When microparticles are used as supports, repertoires of oligonucleotide tags and tag complements may be generated by subunit-wise synthesis via "split and mix" techniques, e.g. as disclosed in Shortle et al, International patent application PCT/US93/03418. Briefly, the basic unit of the synthesis is a subunit of the oligonucleotide tag. Preferably, phosphoramidite chemistry is used and 3' phosphoramidite oligonucleotides are prepared for each subunit in a minimally cross-hybridizing set, e.g. for the set first listed above, there would be eight 4-mer 3'-phosphoramidites. Synthesis proceeds as disclosed by Shortle et al or in direct analogy with the techniques employed to generate diverse oligonucleotide libraries using nucleosidic monomers, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; Lam et al, Nature, 354: 82–84 (1991); Zuckerman et al, Int.

J. Pept. Protein Research, 40: 498–507 (1992); and the like. Generally, these techniques simply call for the application of mixtures of the activated monomers to the growing oligonucleotide during the coupling steps.

If the coupling yields of subunit-wise synthesis is unacceptably low, oligonucleotide tags may also be synthesized monomer-by-monomer by providing separate synthesis chambers for each "word" to be attached. Thus, if a repertoire of tags were based on eight four-nucleotide words, then eight synthesis chambers would be required. After the attachment of a word (by four separate monomer additions in the same chamber), the microparticles are removed from the chambers, mixed, then reallocated to the eight chambers for the synthesis of the next word. The next word is then synthesized in four monomer additions, and the cycle is repeated until the tag is completed.

Double stranded forms of tags may be made by separately synthesizing the complementary strands followed by mixing under conditions that permit duplex formation. Alternatively, double stranded tags may be formed by first synthesizing a single stranded repertoire linked to a known oligonucleotide sequence that serves as a primer binding site. The second strand is then synthesized by combining the single stranded repertoire with a primer and extending with a polymerase. This latter approach is described in Oliphant et al, Gene, 44: 177–183 (1986). Such duplex tags may then be inserted into cloning vectors along with target polynucleotides for sorting and manipulation of the target polynucleotide in accordance with the invention.

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267:5712–5721 (1992); Yoon et al, Proc. Natl. Acad. Sci., 89: 3840–3844 (1992); Blume et al, Nucleic Acids Research, 20: 1777–1784 (1992); Thuong and Helene, Angew. Chem. Int. Ed. Engl. 32: 666–690 (1993); and the like. Conditions for annealing single-stranded or duplex tags to their single-stranded or duplex complements are well known, e.g. Ji et al, Anal. Chem. 65: 1323–1328 (1993).

When oligomeric subunits are employed, oligonucleotide tags of the invention and their complements may range in length from 12 to 60 nucleotides or basepairs; more preferably, they range in length from 18 to 40 nucleotides or basepairs; and most preferably, they range in length from 25 to 40 nucleotides or basepairs. When constructed from antisense monomers, oligonucleotide tags and their complements preferably range in length from 10 to 40 monomers; and more preferably, they range in length from 12 to 30 monomers.

TABLE III

Numbers of Subunits in Tags in Preferred Embodiments

| Monomers in Subunit | Nucleotides in Oligonucleotide Tag | | |
|---|---|---|---|
|  | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags are single stranded and specific hybridization occurs via Watson-Crick pairing with a tag complement.

After chemical synthesis libraries of tags are conveniently maintained as PCR amplicons that include primer binding regions for amplification and restriction endonuclease recognition sites to facilitate excision and attachment to polynucleotides. Preferably, the composition of the primers is selected so that the right and left primers have approximately the same melting and annealing temperatures. In some embodiments, either one or both of the primers and other flanking sequences of the tags consist of three or fewer of the the four natural nucleotides in order to allow the use of a "stripping" and exchange reaction to render a construct containing a tag single stranded in a selected region. Such reactions usually employ the 3'→5' exonuclease activity of a DNA polymerase, such as T4 DNA polymerase, or like enzyme, and are described in Sambrook et al, Molecular Cloning, Second Edition (Cold Spring Harbor Laboratory, New York, 1989).

As mentioned above, an important use of the tags is for "shuttling" information from a target polynucleotide to a solid phase support containing tag complements. Preferably, this step is carried out by excising the tag-containing segment of a double stranded template, e.g. one or more restriction endonucleases, separating it from the reaction mixture, denaturing and labelling the excised tag, and applying it to the solid phase support for detection. This step can be carried out in a variety of ways using standard molecular biological techniques, one of which is exemplified below. Likewise, the excised tags can be labeled in a variety of ways, including the direct or indirect attachment of radioactive moieties, fluorescent moieties, colorimetric moieties, chemiluminescent markers, and the like. Many comprehensive reviews of methodologies for labeling DNA and constructing DNA probes provide guidance applicable to labelling tags of the present invention. Such reviews include Kricka, editor, Nonisotopic DNA Probe Techniques (Academic Press, San Diego, 1992); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Kessler, editor, Nonradioactive Labeling and Detection of Biomolecules (Springer-Verlag, Berlin, 1992); and the like.

Preferably, the tags are labeled with one or more fluorescent dyes, e.g. as disclosed by Menchen et al, U.S. Pat. No. 5,188,934; and Begot et al International application PCT/US90/05565.

Solid Phase Supports for Tag Complements

Preferably, detection of sequence information takes place at spatially discrete locations where tags hybridize to their complements. It is important that the detection of signals from successive cycles of tag transfer be associated with the same tag complement location throughout the sequencing operation. Otherwise, the sequence of signals will not be a faithful representation of the sequence of the polynucleotide corresponding to the tag and tag complement. This requirement is met by providing a spatially addressable array of tag complement. As used herein "spatially addressable" means that the location of a particular tag complement can be recorded and tracked throughout a sequencing operation. Knowledge of the identity of a tag complement is not crucial; it is only important that its location be identifiable from cycle to cycle of tag transfers. Preferably, the regions containing tag complements are discrete, i.e. non-overlapping with regions containing different tag complements, so that signal detection is more convenient. Generally, spatially addressable arrays are constructed by attaching or synthesizing tag complements on solid phase supports.

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of complementary sequences of the same tag (and no other), or a single or a few supports are employed with spacially discrete regions each containing a uniform coating, or population, of complementary sequences to the same tag (and no other). In the latter embodiment, the area of the regions may vary according to particular applications; usually, the regions range in area from several $\mu m^2$, e.g. 3–5, to several hundred $\mu m^2$, e.g. 100–500.

Tag complements may be used with the solid phase support that they are synthesized on, or they may be separately synthesized and attached to a solid phase support for use, e.g. as disclosed by Lund et al, Nucleic Acids Research, 16: 10861–10868 (1988); Albretsen et al, Anal. Biochem., 189: 40–50 (1990); Wolf et al, Nucleic Acids Research, 15: 2911–2926 (1987); or Ghosh et al, Nucleic Acids Research, 15: 5353–5372 (1987). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the tags are used. Exemplary linking moieties are disclosed in Pon et al, Biotechniques, 6:768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1992); and the like. As described more fully below, when tag complements are attached or synthesized on microparticles, populations of microparticles are fixed to a solid phase support to form a spatially addressable array.

As mentioned above, tag complements may also be synthesized on a single (or a few) solid phase support to form an array of regions uniformly coated with tag complements. That is, within each region in such an array the same tag complement is synthesized. Techniques for synthesizing such arrays are disclosed in McGall et al, International application PCT/US93/03767; Pease et al, Proc. Natl. Acad. Sci., 91: 5022–5026 (1994); Southern and Maskos, International application PCT/GB89/01114; Maskos and Southern (cited above); Southern et al, Genomics, 13: 1008–1017 (1992); and Maskos and Southern, Nucleic Acids Research, 21: 4663–4669 (1993).

Preferably, the invention is implemented with microparticles or beads uniformly coated with complements of the same tag sequence. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 $\mu m$ diameter are preferable, as they facilitate the construction and manipulation of large repertoires of oligonucleotide tags with minimal reagent and sample usage.

Preferably, commercially available controlled-pore glass (CPG) or polystyrene supports are employed as solid phase supports in the invention. Such supports come available with base-labile linkers and initial nucleosides attached, e.g. Applied Biosystems (Foster City, Calif.). Preferably, microparticles having pore size between 500 and 1000 angstroms are employed.

In other preferred applications, non-porous microparticles are employed for their optical properties, which may be advantageously used when tracking large numbers of microparticles on planar supports, such as a microscope slide. Particularly preferred non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of tagged microparticles, 5 $\mu m$ diameter GMA beads are employed.

Attaching Tags to Target Polynucleotides

An important aspect of the invention is tagging of polynucleotides of a population, e.g. a cDNA library, such that the same tag is not attached to different polynucleotides.

This latter condition can be essentially met by ligating a repertoire of tags to a population of polynucleotides followed by cloning and sampling of the ligated sequences. A repertoire of oligonucleotide tags can be ligated to a population of polynucleotides in a number of ways, such as through direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, by taking a sufficiently small sample of the conjugates, the probability of obtaining "doubles," i.e. the same tag on two different polynucleotides, can be made negligible. (Note that it is also possible to obtain different tags with the same polynucleotide in a sample. This case simply leads to a polynucleotide being processed, e.g. sequenced, twice. Also, where patterns of gene expression are being analyzed, multiple tags with the same polynucleotide will be a common occurence—and expected—because of differences in mRNA abundances). As explain more fully below, the probability of obtaining a double in a sample can be estimated by a Poisson distribution since the number of conjugates in a sample will be large, e.g. on the order of thousands or more, and the probability of selecting a particular tag will be small because the tag repertoire is large, e.g. on the order of tens of thousand or more. Preferably, the size of the tag repertoire is about 100 times the number of distinct species of polynucleotide in the population being analyzed. Or, in other words, the complexity of the tag repertoire is preferably about 100 times that of the population of polynucleotides being analyzed. Generally, the larger the sample the greater the probability of obtaining a double. Thus, a design trade-off exists between selecting a large sample of tag-polynucleotide conjugates— which, for example, ensures adequate coverage of a target polynucleotide in a shotgun sequencing operation, and selecting a small sample which ensures that a minimal number of doubles will be present. In most embodiments, the presence of doubles merely adds an additional source of noise or, in the case of sequencing, a minor complication in scanning and signal processing, as regions of tag complements simultaneously giving multiple signals can simply be ignored. As used herein, the term "substantially all" in reference to attaching tags to polynucleotides is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the tags have unique polynucleotides attached. More preferably, it means that at least ninety percent of the tags have unique polynucleotides attached. Still more preferably, it means that at least ninety-five percent of the tags have unique polynucleotides attached. And, most preferably, it means that at least ninety-nine percent of the tags have unique polynucleotides attached.

In a preferred embodiment, tags, polynucleotides to be sequenced, primer binding sites, and other elements for manipulating the sequences are inserted into a cloning vector to establish a base library that may be sampled and amplified as needed. For example, such a construct could have the following form:

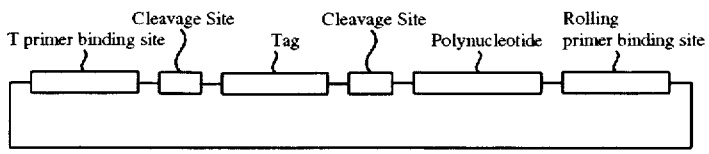

where the "T" or tag primer binding site and the "S" or sequencing primer binding site are used with the appropriate primers to amplify the insert of the cloning vector to form PCR amplicons for subsequent analysis. The cleavage sites are used to excise the tag from the amplicons, after steps of PCR amplification and identification of a terminal nucleotide. As noted below, after amplifications, it is important that the target polynucleotides be protected from undesired cleavage by the nucleases employed in the identification step. Preferably, this is accomplished by methylation and careful selection of restriction endonucleases.

Sequencing Tagged Polynucleotides

Figure 2A:
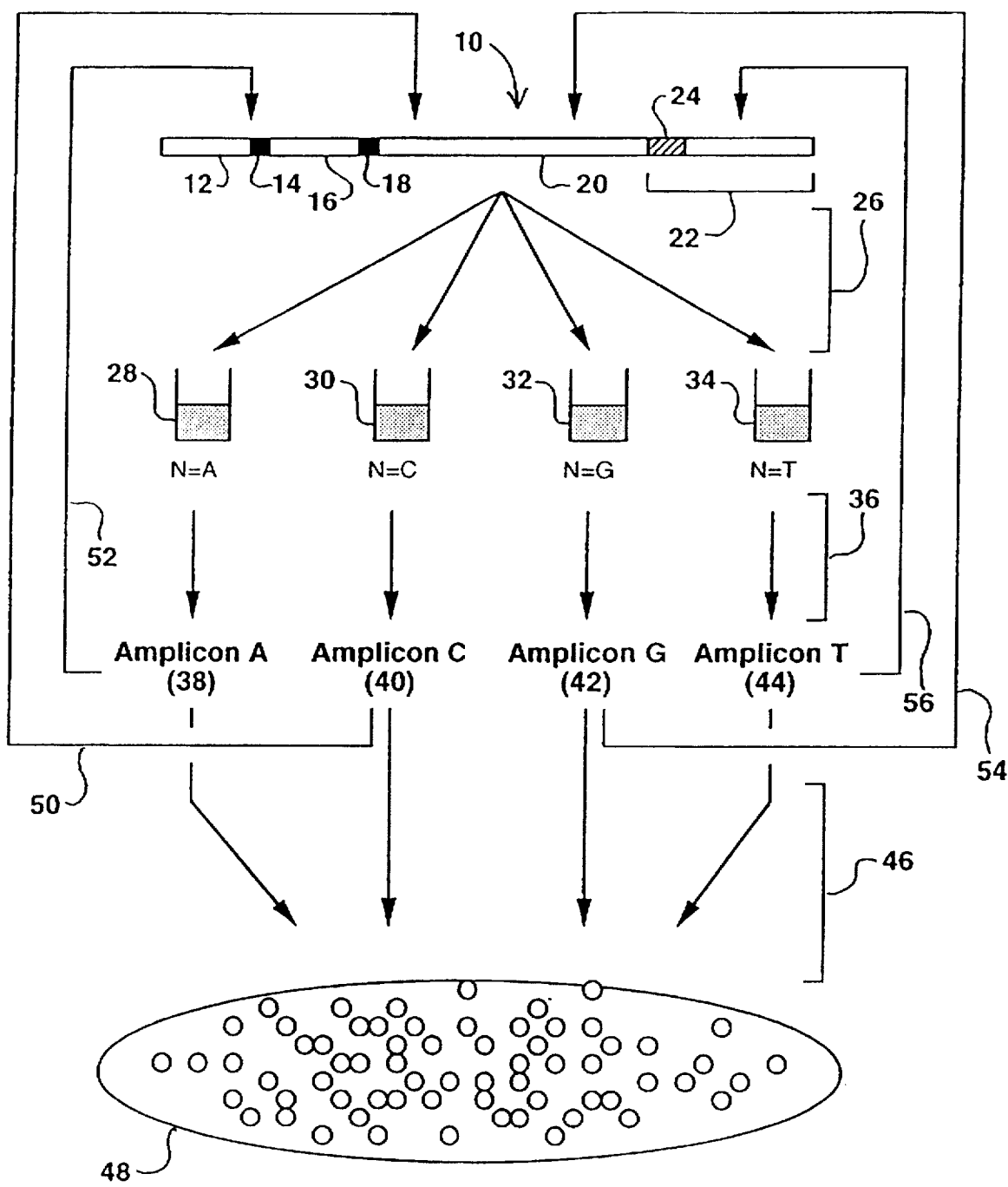
FIG. 2a diagrammatically illustrates the steps of a preferred method of the invention.

A preferred embodiment for simultaneously sequencing a population of tagged polynucleotides is diagrammed in FIG. 2a. Preferably, the population of tagged polynucleotides is amplified from a vector as described above in the presence of dATP, dCTP, dITP, and dTTP to give a population of double stranded DNAs (10) containing T primer binding site (12), cleavage site (14)—which as shown below is optional, tag (16), cleavage site (18), target polynucleotides (20), and rolling primer binding site (22).

In the initial population, rolling primer binding site (22) contains a known complement to the extension region (24), for example, AGG as shown in the example below. Samples of the initial population are preferably transferred (26) to four separate vessels (28–34) where they are combined with the rolling primers of subgroup (1), described above, having extension regions —AIIA, —AIIC, —AIIG, and —AIIT. (The four rolling primer could be placed in a single vessel and allowed to compete against one another for extension; however, errors are less likely if the primers are used separately). The rolling primers of subgroups (1)–(6) are used here to exemplify the invention. Clearly, many alternative forms of the rolling primers could be used. In subsequent cycles, as described more fully below, the transferring step (26) becomes more complex because more than four vessels, i.e. up to 32 (=4×8) in the embodiment exemplified here, are required for the extension reactions. After the double stranded DNAs (10) are combined with the appropriate rolling primers the following steps (36) are taken: the double stranded DNAs are denatured, e.g. by heating; the temperature is lowered to permit the rolling primers to anneal to the rolling primer binding sites; the primers are extended with a high fidelity DNA polymerase, such as Sequenase, in the presence of dATP, dCTP, dITP, and dTTP; preferably, any remaining single stranded DNA is digested, e.g. with a single stranded nuclease, such as Mung bean nuclease, to reduce the likelihood of interference from the left over single stranded DNA in the subsequent amplification; T primer is added; and the double stranded extension products are amplified, preferably with 5–10 cycles of PCR, to generate amplicon A (38), amplicon C (40), amplicon G (42), and amplicon T (44), respectively.

As an alternative, and/or supplement, to the step of digesting with a single stranded nuclease, the double stranded DNA (10) can be treated with a methylase (or equivalently, amplified in the presence of 5-methylcytosine triphosphate). After such treatment, any double stranded DNA that is not the product of at least two extension reactions will be hemi-methylated or fully methylated at cleavage site (18). Thus, a nuclease that recognizes site (18) on those sequences will not cleave it. If a sample of amplicon is taken by way of a capture agent, such as biotin, on the T primer, tags may be release for analysis by cleaving with the nuclease for cleavage site (18). However, those sites that are methylated or hemi-methylated will not be cleaved to give a spurious signal upon application of the tags to a solid phase support (48).

After a sample is taken from each amplicon, tags are excised by way of cleavage sites (14) and/or (18) and labeled (46), as described more fully below. The labeled tags are then either applied separately to their tag complements on solid phase support (48) or pooled and applied to the support, depending on the labeling system employed, the complexity of the tag mixture, and like factors. Samples of the amplicons are also taken for further processing (50–56) in accordance with the method of the invention. Depending on the identity of the most recently determined nucleotide and the identity of the current extension region, a sample either may be separately aliquotted into vessels with rolling primers for the next cycle, or a sample may be combined with one or more other samples and aliquotted into vessels with rolling primers for the next cycle. Unlike the single polynucleotide case, when a population of polynucleotides is sequenced every vessel will almost always contain an amplicon at the conclusion of the amplification reaction. Thus, after extension, digestion, and amplification, the amplicons in the vessels 28, 30, 32, and 34 correspond to target polynucleotides having a T, G (or I), C, and A at their initial positions (or more generally, at the nucleotide position adjacent to the rolling primer binding site), respectively. With this information, and a knowledge of the sequence of the extension region of the current amplicon, the rolling primers of the next cycle can be selected. As in the single polynucleotide case, in each successive cycle a rolling primer is selected that shifts, or advances, the rolling primer binding site one or more nucleotides along the template in the direction of rolling primer extension. Preferably, a single nucleotide shift takes place in each cycle. As described above, the rolling primers selected for the extension step also serve to generate a mutation in the template upon amplification. The mutation changes the interior-most nucleotide of the extension region to one that is complementary to the template positioning segment of the rolling primer of the current cycle. In the tables below, the pattern of primer selection and amplicon pooling in cycles 2 through 4 of a sequencing operation is illustrated for the above embodiment. In the first cycle, the original template is distributed to four vessels for denaturation and extension.

| Selection of Rolling Primers for 2nd Cycle | | | |
|---|---|---|---|
| Amplicon | Sequence adjacent to primer binding site | Extension region of next rolling primer | Extension regions of merged or combined primers |
| A | ...I I AIA... <br> ...CCTIT... | -> IAA | -IAAA <br> -IAAC <br> -IAAG <br> -IAAT |
| C | ...I I AIC... <br> ...CCTII... | -> IAA | |
| G | ...I I AIG... <br> ...CCTIC... | -> IAI | -IAIA <br> -IAIC <br> -IAIG <br> -IAIT |
| T | ...I I AIT... <br> ...CCTIA... | -> IAI | |

Figure 2B:
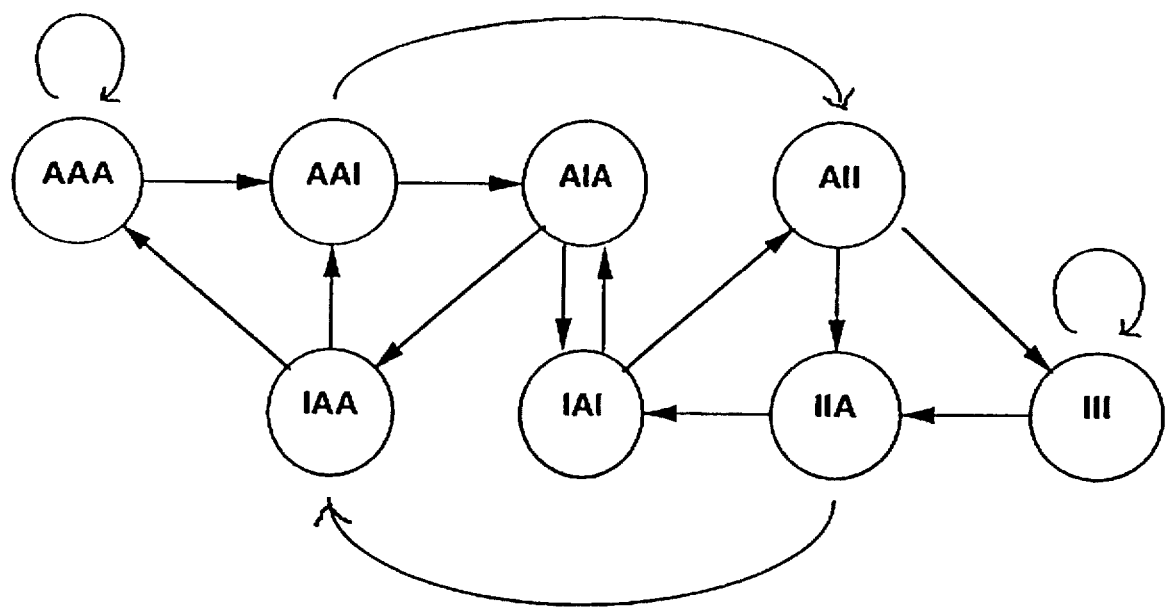
FIG. 2b illustrates the extension regions of rolling primers for subsequent steps that are selected based on the identity of the rolling primer extension region of the current step.

The nucleotide to the right of the line between nucleotides in the second column is the terminal nucleotide of the rolling primer used to produce the amplicon. Generally, the algorithm for determining the rolling primers of the next cycle is as follows: (i) drop the nucleotide distal to the terminal nucleotide in the extension region of the current rolling primer (the leftmost "I" of the "IIA" sequences in the second column), (ii) determine which nucleotide, I or A, is complementary to the nucleotide paired with the terminal nucleotide (i.e. for the above example: "A" for amplicon A, "A" for amplicon C—since A will pair with I as well as T, "I" for amplicon G—since I will pair with C, and "I" for amplicon T—since I will also pair with A), (iii) insert the determined nucleotide, I or A, to the left of the terminal nucleotide. For this embodiment, the general pattern of transitions between extension region sequences is illustrated in FIG. 2b. Longer extension regions lead to more complex patterns, but the basic algorithm defining permissible transitions remains the same.

| Selection of Rolling Primers for 3rd Cycle | | | |
|---|---|---|---|
| Amplicon | Sequence adjacent to primer binding site | Extension region of next rolling primer | Extension regions of merged or combined primers |
| $A_1$ | ...I AAIA... <br> ...CTTIT... | -> AAA | -AAAA <br> -AAAC <br> -AAAG <br> -AAAT |
| $A_2$ | ...I AI IA... <br> ...CTCIT... | -> AI A | |
| $C_1$ | ...I AAIC... <br> ...CTTII... | -> AAA | -AI AA <br> -AI AC <br> -AI AG <br> -AI AT |
| $C_2$ | ...I AI IC... <br> ...CTCII... | -> AI A | |
| $G_1$ | ...I AAIG... <br> ...CTTIC... | -> AAI | -AAI A <br> -AAI C <br> -AAI G <br> -AAI T |
| $G_2$ | ...I AI IG... <br> ...CTCIC... | -> AI I | |
| $T_1$ | ...I AAIT... <br> ...CTTIA... | -> AAI | -AI I A <br> -AI I C <br> -AI I G <br> -AI I T |
| $T_2$ | ...I AI IT... <br> ...CTCIA... | -> AI I | |

Selection of Rolling Primers for 4th Cycle

| Amplicon | Sequence adjacent to primer binding site | Extension region of next rolling primer | Extension regions of merged or combined primers |
|---|---|---|---|
| $A_1$ | ...AAA IA... -><br>...TTT IT ... | AAA | -AAAA<br>-AAAC<br>-AAAG<br>-AAAT |
| $A_2$ | ...AI AIA... -><br>...TCT IT ... | I AA | |
| $A_3$ | ...AAI IA... -><br>...TTC IT ... | AI A | -I AAA<br>-I AAC<br>-I AAG<br>-I AAT |
| $A_4$ | ...AI I IA... -><br>...TCC IT ... | II A | -AI AA<br>-AI AC<br>-AI AG<br>-AI AT |
| $C_1$ | ...AAA IC... -><br>...TTT II ... | AAA | |
| $C_2$ | ...AI AIC... -><br>...TCT II ... | I AA | |
| $C_3$ | ...AAI IC... -><br>...TTC II ... | AI A | -II AA<br>-II AC<br>-II AG<br>-II AT |
| $C_4$ | ...AI I IC... -><br>...TCC II ... | II A | |
| $G_1$ | ...AAA IG... -><br>...TTT IC ... | AAI | -AAI A<br>-AAI C<br>-AAI G<br>-AAI T |
| $G_2$ | ...AI AIG... -><br>...TCT IC ... | I AI | |
| $G_3$ | ...AAI IG... -><br>...TTC IC ... | AI I | -I AI A<br>-I AI C<br>-I AI G<br>-I AI T |
| $G_4$ | ...AI I IG... -><br>...TCC IC ... | I I I | -AI I A<br>-AI I C<br>-AI I G<br>-AI I T |
| $T_1$ | ...AAA IT ... -><br>...TTT IA... | AAI | |
| $T_2$ | ...AI AIT ... -><br>...TCT IA... | I AI | -III A<br>-III C<br>-III G<br>-III T |
| $T_3$ | ...AAI IT ... -><br>...TTC IA... | AI I | |
| $T_4$ | ...AI I IT ... -><br>...TCC IA... | I I I | |

Typically, by the eighth cycle thirty-two reactions are required, and continue to be required, in each cycle until sequencing is halted.

Clearly, additional steps to those outlined above may be implemented, for example, to separate the initial extension product from extraneous single stranded DNA and/or the single stranded nuclease, if one is employed. Manipulation of polynucleotides and other reagents, temperature control for PCRs, and the like, may be carried out on commercially available laboratory robots, e.g. Biomek 1000 (Beckman Instruments, Fullerton, Calif.).

Rolling primers and T primers may be constructed to have a double stranded segment capable of binding to an anchored single stranded oligonucleotide via triplex formation for separation, e.g. as taught by Ji et al, Anal. Chem. 65: 1323–1328 (1993); Cantor et al, U.S. Pat. No. 5,482,836; or the like. Thus, for example, magnetic beads carrying such a single stranded oligonucleotide can be used to capture the amplicons and transfer them to a separate vessel containing a nuclease to cleave the tag, e.g. at cleavage site 18, of those double stranded DNAs that have been selectively amplified (other DNAs remain unamplified and therefore hemimethylated so no cleavage occurs). Preferably, the T primer contains a 5' biotin which permits the released tag to be captured and conveniently labeled. After capture, e.g. via avidinated magnetic beads, the 3' strands of the double stranded segment are stripped back to the tag by the use of T4 DNA polymerase, or like enzyme, in the presence of a deoxynucleoside triphosphate (dNTP) corresponding to the nucleotide flanking the tag. Thus, provided that the flanking nucleotides are not present elsewhere along the strand to the 3' ends, the 3'→5' exonuclease activity of the polymerase will strip back the 3' strand to the flanking nucleotides, at which point an exchange reaction will be initiated that prevents further stripping past the flanking nucleotides. The 3' ends of the tag can then be labeled in an extension reaction with labeled dNTPs. After labeling the non-biotinylated strand can be removed by denaturation and applied to the spatially addressable array for detection.

After the labeled tags are hybridized to their tag complements and detected, the tags are removed by washing so that labeled tags from the next set of amplicons can be applied.

Apparatus for Observing Detection Signals at Spatially Addressable Sites

Preferably, a spatially addressable array is established by fixing microparticle containing tag complements to a solid phase surface.

Preferably, whenever light-generating signals, e.g. chemiluminescent, fluorescent, or the like, are employed to detect tags, microparticles are spread on a planar substrate, e.g. a glass slide, for examination with a scanning system, such as described in International patent applications PCT/US91/09217, PCT/NL90/00081, and PCT/US95/01886. The scanning system should be able to reproducibly scan the substrate and to define the positions of each microparticle in a predetermined region by way of a coordinate system. In polynucleotide sequencing applications, it is important that the positional identification of microparticles be repeatable in successive scan steps.

Figure 3:
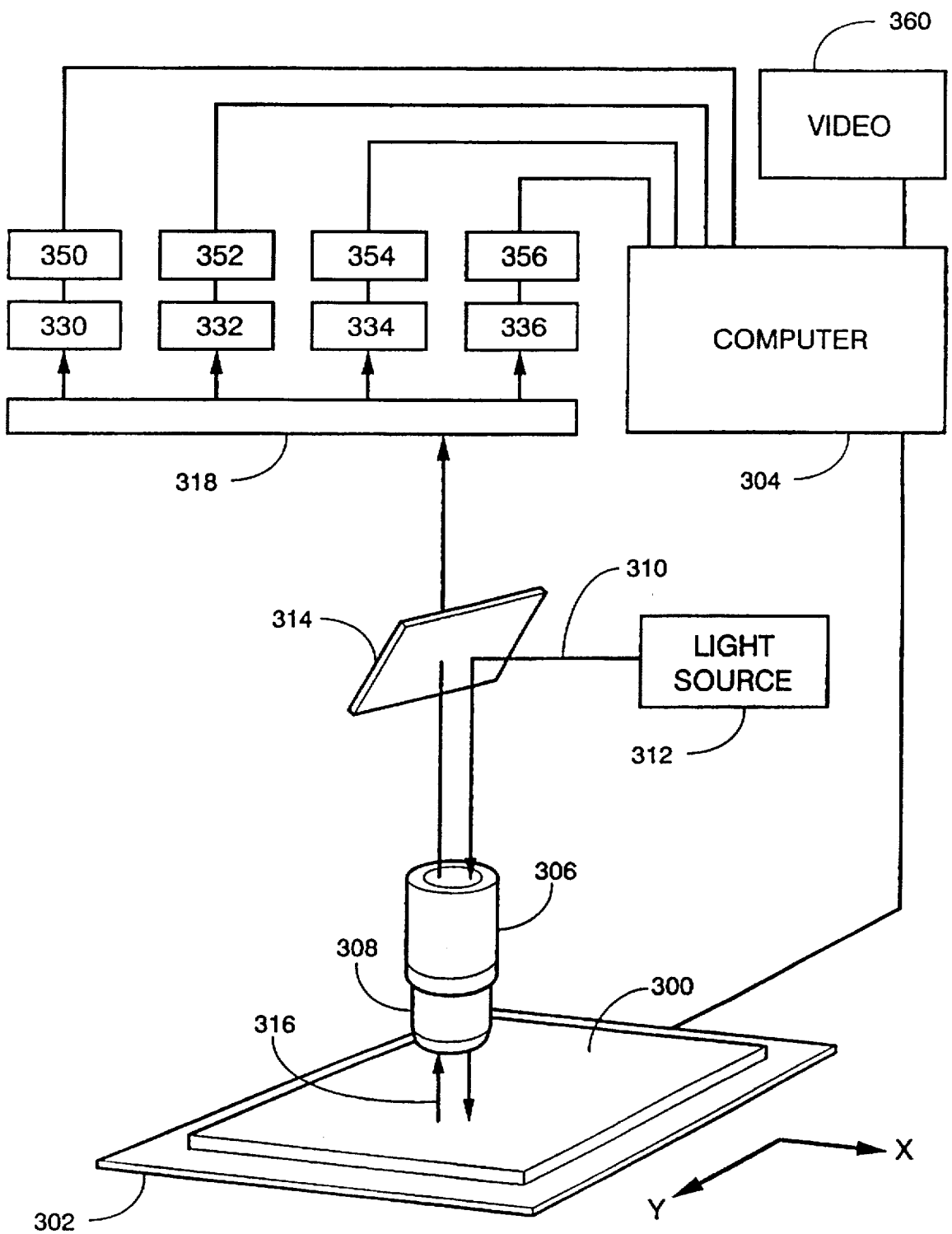
FIG. 3 diagrammatically illustrates an apparatus for detecting labeled tags on a spatially addressable array of tag complements.

Such scanning systems may be constructed from commercially available components, e.g. x–y translation table controlled by a digital computer used with a detection system comprising one or more photomultiplier tubes, or alternatively, a CCD array, and appropriate optics, e.g. for exciting, collecting, and sorting fluorescent signals. In some embodiments a confocal optical system may be desirable. An exemplary scanning system suitable for use in four-color sequencing is illustrated diagrammatically in FIG. 3. Substrate 300, e.g. a microscope slide with fixed microparticles, is placed on x–y translation table 302, which is connected to and controlled by an appropriately programmed digital computer 304 which may be any of a variety of commercially available personal computers, e.g. 486-based machines or PowerPC model 7100 or 8100 available form Apple Computer (Cupertino, Calif.). Computer software for table translation and data collection functions can be provided by commercially available laboratory software, such as Lab Windows, available from National Instruments.

Substrate 300 and table 302 are operationally associated with microscope 306 having one or more objective lenses 308 which are capable of collecting and delivering light to microparticles fixed to substrate 300. Excitation beam 310 from light source 312, which is preferably a laser, is directed to beam splitter 314, e.g. a dichroic mirror, which re-directs the beam through microscope 306 and objective lens 308 which, in turn, focuses the beam onto substrate 300. Lens 308 collects fluorescence 316 emitted from the microparticles and directs it through beam splitter 314 to signal distribution optics 318 which, in turn, directs fluorescence to one or more suitable opto-electronic devices for converting some fluorescence characteristic, e.g. intensity, lifetime, or the like, to an electrical signal. Signal distribution optics 318 may comprise a variety of components standard in the art, such as bandpass filters, fiber optics, rotating mirrors, fixed position mirrors and lenses, diffraction gratings, and the like. As illustrated in FIG. 5, signal distribution optics 318 directs fluorescence 316 to four separate photomultiplier tubes, 330, 332, 334, and 336, whose output is then directed to pre-amps and photon counters 350, 352, 354, and 356. The output of the photon counters is collected by computer 304, where it can be stored, analyzed, and viewed on video 360. Alternatively, signal distribution optics 318 could be a diffraction grating which directs fluorescent signal 318 onto a CCD array.

The stability and reproducibility of the positional localization in scanning will determine, to a large extent, the resolution for separating closely spaced microparticles. Preferably, the scanning systems should be capable of resolving closely spaced microparticles, e.g. separated by a particle diameter or less. Thus, for most applications, e.g. using CPG microparticles, the scanning system should at least have the capability of resolving objects on the order of 5–100 nm. Even higher resolution may be desirable in some embodiments, but with increase resolution, the time required to fully scan a substrate will increase; thus, in some embodiments a compromise may have to be made between speed and resolution. Increases in scanning time can be achieved by a system which only scans positions where microparticles are known to be located, e.g from an initial full scan. Preferably, microparticle size and scanning system resolution are selected to permit resolution of fluorescently labeled microparticles randomly disposed on a plane at a density between about ten thousand to one hundred thousand microparticles per cm².

In sequencing applications, microparticles can be fixed to the surface of a substrate in variety of ways. The fixation should be strong enough to allow the microparticles to undergo successive cycles of reagent exposure and washing without significant loss. When the substrate is glass, its surface may be derivatized with an alkylamino linker using commercially available reagents, e.g. Pierce Chemical, which in turn may be cross-linked to avidin, again using conventional chemistries, to form an avidinated surface. Biotin moieties can be introduced to the microparticles in a number of ways.

In an alternative, when DNA-loaded microparticles are applied to a glass substrate, the DNA nonspecifically adsorb to the glass surface upon several hours, e.g. 24 hours, incubation to create a bond sufficiently strong to permit repeated exposures to reagents and washes without significant loss of microparticles. Such a glass substrate may be a flow cell, which may comprise a channel etched in a glass slide. Preferably, such a channel is closed so that fluids may be pumped through it and has a depth sufficiently close to the diameter of the microparticles so that a monolayer of microparticles is trapped within a defined observation region.

Kits for Implementing the Method of the Invention

The invention includes kits for carrying out the various embodiments of the invention. Preferably, kits of the invention include a set of rolling primers for carrying out the extensions and amplifications in accordance with the invention. Kits may also include a repertoire of tag complements attached to a solid phase support. Additionally, kits of the invention may include the corresponding repertoire of tags, e.g. as primers for amplifying the polynucleotides to be sorted or as elements of cloning vectors. Preferably, the repertoire of tag complements are attached to microparticles. Kits may also contain appropriate buffers for enzymatic processing, detection chemistries, e.g. fluorescent or chemiluminescent components for labelling tags, and the like, instructions for use, processing enzymes, such as ligases, polymerases, transferases, and so on. In an important embodiment for sequencing, kits may also include substrates, such as a avidinated microscope slides or microtiter plates, for fixing microparticles for processing.

Example 1

Construction of a Tag Library

An exemplary tag library is constructed as follows to form the chemically synthesized 9-word tags of nucleotides A, G, and T defined by the formula:

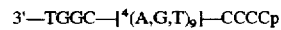

3'—TGGC—[*(A,G,T)₉]—CCCCp where "[*((A,G,T)₉]" indicates a tag mixture where each tag consists of nine 4-mer words of A, G, and T; and "p" indicate a 5' phosphate. This mixture is ligated to the following right and left primer binding regions (SEQ ID NO:8 and SEQ ID NO:9):

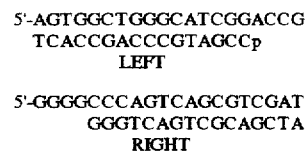

5'-AGTGGCTGGGCATCGGACCG
TCACCGACCCGTAGCCp
LEFT

5'-GGGGCCCAGTCAGCGTCGAT
GGGTCAGTCGCAGCTA
RIGHT

The right and left primer binding regions are ligated to the above tag mixture, after which the single stranded portion of the ligated structure is filled with DNA polymerase then mixed with the right and left primers indicated below and amplified to give a tag library.

Left Primer

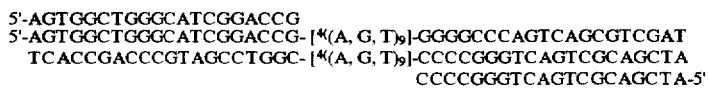

5'-AGTGGCTGGGCATCGGACCG
5'-AGTGGCTGGGCATCGGACCG-[*(A, G, T)₉]-GGGGCCCAGTCAGCGTCGAT
TCACCGACCCGTAGCCTGGC-[*(A, G, T)₉]-CCCCGGGTCAGTCGCAGCTA
                                    CCCCGGGTCAGTCGCAGCTA-5'

Right Primer

The underlined portion of the left primer binding region indicates a Rsr II recognition site. The left-most underlined region of the right primer binding region indicates recognition sites for Bsp 120I, Apa I, and Eco O 109I, and a cleavage site for Hga I. The right-most underlined region of the right primer binding region indicates the recognition site for Hga I. Optionally, the right or left primers may be synthesized with a biotin attached (using conventional reagents, e.g. available from Clontech Laboratories, Palo Alto, Calif.) to facilitate purification after amplification and/or cleavage.

Example 2

Construction of a Plasmid Library of Tag-Polynucleotide Conjugates for cDNA "Signature" Sequencing cDNA is produced from an mRNA sample by conventional protocols using pGGCCCT$_{15}$(A or G or C) as a primer for first strand synthesis anchored at the boundary of the poly A region of the mRNAs and N$_8$(A or T)GATC as the primer for second strand synthesis. That is, both are degenerate primers such that the second strand primer is present in two forms and the first strand primer is present in three forms. The GATC sequence in the second strand primer corresponds to the recognition site of Mbo I; other four base recognition sites could be used as well, such as those for Bam HI, Sph I, Eco RI, or the like. The presence of the A and T adjacent to the restriction site of the second strand primer ensures that a stripping and exchange reaction can be used in the next step to generate a five-base 5' overhang of "GGCCC". The first strand primer is annealed to the mRNA sample and extended with reverse transcriptase, after which the RNA strand is degraded by the RNase H activity of the reverse transcriptase leaving a single stranded cDNA. The second strand primer is annealed and extended with a DNA polymerase using conventional protocols. After second strand synthesis, the resulting cDNAs are methylated with CpG methylase (New England Biolabs, Beverly, Mass.) using manufacturer's protocols. The 3' strands of the cDNAs are then cut back with the above-mentioned stripping and exchange reaction using T4 DNA polymerase in the presence of dATP and dTTP, after which the cDNAs are ligated to the tag library of Example 1 previously cleaved with Hga I to give the following construct:

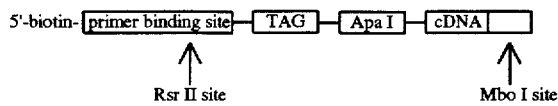

Separately, the following cloning vector (SEQ ID NO:10) is constructed, e.g. starting from a commercially available plasmid, such as a Bluescript phagemid (Stratagene, La Jolla, Calif.).

The rolling primer binding site corresponds to a rolling primer of subgroup (1), described above. The plasmid is cleaved with Ppu MI and Pme I (to give a Rsr II-compatible end and a flush end so that the insert is oriented) and then methylated with DAM methylase. The tag-containing construct is cleaved with Rsr II and then ligated to the open plasmid, after which the conjugate is cleaved with Mbo I and Bam HI to permit ligation and closing of the plasmid. The plasmid is then amplified and isolated for use as a template for extensions and amplifications in accordance with the invention.

Example 3

Signature Sequencing of a cDNA Library

The plasmid constructed in Example 2 is used for generating extension products and amplicons with the rolling primers described above and the following T primer (SEQ ID NO:11):

biotin-5'-IIIIIIIAAAAGGAGGAGGCCTTGA where the I's are deoxyinosines added to balance the annealing and melting temperatures of the T primers and rolling primers. Preferably, the annealing temperature is about 55° C. Clearly, many other sequences could be employed in the implementation of the invention. The rolling primers described above are employed.

The segment containing the T primer binding site through the rolling primer binding site is excised and separated from the plasmid of example 2. (This can be accomplish in a variety of ways know to those skilled in the art, for example, engineering the plasmid to contain restriction sites flanking the segment, or by simply amplifying directly by PCR). After replacing deoxyguanosines with deoxyinosines, e.g. by PCR in the presence of dITP, the segment is aliquotted into four vessels, denatured, and the appropriate rolling primer is added. Conditions are adjusted to permit the rolling primers to anneal, after which the primers are extended with Sequenase, or like high fidelity polymerase, in the presence of dATP, dCTP, dITP, and dTTP, using the manufacturer's protocol. The remaining single stranded DNA is digested with a single stranded nuclease, such as Mung bean nuclease. Optionally, the double stranded DNA extension product may be separated from the reaction mixture, e.g. by capture via the formation of a triplex between, for example, the T primer binding region, and an appropriate single stranded complement attached to a magnetic bead.

The double stranded DNA is combined with T primer (and rolling primer if a separation step was used) and amplified

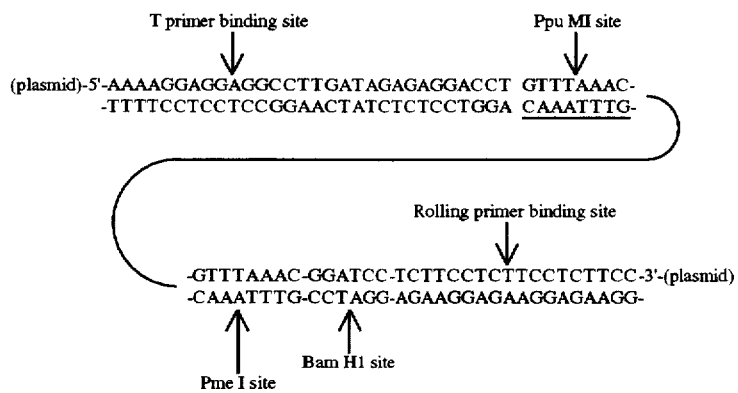

by 5-10 cycles of PCR in the presence of dATP, dCTP, dITP, and dTTP to form the four initial amplicons. Samples of these are combined and re-distributed into vessels with the appropriate rolling primers for the next cycle of extension. Samples are also drawn off for analysis.

Preferably, the samples for analysis are separately captured on magnetic beads carrying a single stranded sequence that forms a triplex with the S primers. The beads are then transferred to reaction mixtures containing Apa I, which cleaves the tags from the target polynucleotide. The released strands (SEQ ID NO:12) containing the tags are next captured via their biotinylated T primers with magnetic beads coated with avidin and transferred to reaction vessels where their 3' ends are stripped in the presence of T4 DNA polymerase and dGTP, as shown below:

After cleavage with Apa I:

biotin-5'-I I I I I I I I |AG|₁₂TAGAGAGGACCG| TAGS |GGGGCC
            CCCCCCCC|TC|₁₂ATCTCTCCTGGC| SGAT |CC ↓ T4 polymerase + dGTP biotin-5'-I I I I I I I I |AG|₁₂TAGAGAGGACCG| TAGS |GG
                                       GGC| SGAT |CC ↓ Add dUTP*, dCTP & ddATP biotin-5'-I I I I I I I I |AG|₁₂TAGAGAGGACCG| TAGS |GG
                        dAUCUCUCCUGGC| SGAT |CC
                        *   *   *   *

↓ Heat denature dAUCUCUCCUGGC| SGAT |CC-5'
*   *   *   *

Here dUTP* represents a labeled dUTP and ddATP represents dideoxyadenosine triphosphate. Preferably, dUTP is labeled with a separate spectrally resolvable fluorescent dye for each of the four amplicons. The released tags (SEQ ID NO:13) for each of the amplicaon are mixed and are applied to the spatially addressable array for hybridization to their complements and detection.

APPENDIX I

Exemplary computer program for generating minimally cross hybridizing sets

```
Program minxh
c
c
c
        integer*2 sub1(6),mset1(1000,6),mset2(1000,6)
        dimension nbase(6)
c
c
        write(*,*)'ENTER SUBUNIT LENGTH'
        read(*,100)nsub
100     format(i1)
        open(1,file='sub4.dat',form='formatted',status='new')
c
c
        nset=0
        do 7000 m1=1,3
         do 7000 m2=1,3
          do 7000 m3=1,3
           do 7000 m4=1,3
            sub1(1)=m1
            sub1(2)=m2
```

APPENDIX I-continued

Exemplary computer program for generating minimally cross hybridizing sets

```
            sub1(3)=m3
            sub1(4)=m4
c
c
  ndiff=3
c
c
c             Generate set of subunits differing from
c             sub1 by at least ndiff nucleotides.
c             Save in mset1.
c
c
  jj=1
  do 900 j=1,nsub
900    mset1(1,j)=sub1(j)
c
c
       do 1000 k1=1,3
        do 1000 k2=1,3
         do 1000 k3=1,3
          do 1000 k4=1,3
c
c
           nbase(1)=k1
           nbase(2)=k2
           nbase(3)=k3
           nbase(4)=k4
c
       n=0
       do 1200 j=1,nsub
        if(sub1(j).eq.1 .and. nbase(j).ne.1 .or.
1         sub1(j).eq.2 .and. nbase(j).ne.2 .or.
3         sub1(j).eq.3 .and. nbase(j).ne.3) then
           n=n+1
          endif
1200   continue
c
c
       if(n.ge.ndiff) then
c
c
c                                  If number of mismatches
c                                  is greater than or equal
c                                  to ndiff then record
c                                  subunit in matrix mset
c
c
         jj=jj+1
         do 1100 i=1,nsub
1100       mset1(jj,i)=nbase(i)
         endif
c
c
1000   continue
c
c
       do 1325 j2=1,nsub
       mset2(1,j2)=mset1(1,j2)
1325   mset2(2,j2)=mset1(2,j2)
c
c
c                                  Compare subunit 2 from
c                                  mset1 with each successive
c                                  subunit in mset1, i.e. 3,
c                                  4,5, . . . etc. Save those
c                                  with mismatches .ge. ndiff
c                                  in matrix mset2 starting at
c                                  position 2.
c                                   Next transfer contents
c                                  of mset2 into mset1 and
c                                  start
c                                  comparisons again this time
c                                  starting with subunit 3.
c                                  Continue until all subunits
c                                  undergo the comparisons.
c
```

APPENDIX I-continued

Exemplary computer program for generating minimally cross hybridizing sets

```
c
        npass=0
c
c
1700    continue
        kk=npass+2
        npass=npass+1
c
c
        do 1500 m=npass+2,jj
        n=0
        do 1600 j=1,nsub
        if(mset1(npass+1,j).eq.1.and.mset1(m,j).ne.1.or.
    2       mset1(npass+1,j).eq.2.and.mset1(m,j).ne.2.or.
    2       mset1(npass+1,j).eq.3.and.mset1(m,j).ne.3) then
        n=n+1
        endif
1600    continue
        if(n.ge.ndiff) then
        kk=kk+1
        do 1625 i=1,nsub
1625    mset2(kk,i)=mset1(m,i)
        endif
1500    continue
c
c
c                       kk is the number of subunits
c                       stored in mset2
c
c
```

APPENDIX I-continued

Exemplary computer program for generating minimally cross hybridizing sets

```
c                       Transfer contents of mset2
c                       into mset1 for next pass.
c
c
        do 2000 k=1,kk
        do 2000 m=1,nsub
2000    mset1(k,m)=mset2(k,m)
        if(kk.lt.jj) then
        jj=kk
        goto 1700
        endif
c
c
        nset=nset+1
        write(1,7009)
7009    format(/)
        do 7008 k=1,kk
7008    write(1,7010)(mset1(k,m),m=1,nsub)
7010    format(4i1)
        write(*,*)
        write(*,120) kk,nset
120     format(1x,'Subunits in set=',i5,2x,'Set No=',i5)
7000    continue
        close(1)
c
c
        end
```

---

I claim:

1. A method for determining the nucleotide sequence of a polynucleotide, the method comprising the steps of:

(a) providing a set of primers, each primer of the set having a terminal nucleotide, a template positioning segment, and an extension region comprising one or more complexity-reducing nucleotides;

(b) forming a template comprising a primer binding site and the polynucleotide, the primer binding site being complementary to at least one primer of the set;

(c) forming an amplicon from the template by amplifying a double stranded DNA selectively formed by extending a primer from the set whose extension region forms a perfectly matched duplex with the primer binding site of the template;

(d) identifying the terminal nucleotide of the extension region of the primer by the identity of the amplicon;

(e) mutating the primer binding site of the template so that the primer binding site is shifted one nucleotide in the direction of extension; and (f) repeating steps (c) through (e) until the nucleotide sequence of the polynucleotide is determined.

2. The method of claim 1 wherein said amplicon is formed by amplifying said double stranded DNA by a polymerase chain reaction.

3. The method of claim 2 wherein said complexity-reducing nucleotide is deoxyinosine and wherein said polymerase chain reaction and said extending to form said double stranded DNA are carried out in the presence of deoxyadenosine triphosphate, deoxycytidine triphosphate, deoxyinosine triphosphate, and thymidine triphosphate.

4. The method of claim 3 wherein said step of mutating said primer binding site of said template is carried out by extending and amplifying said double stranded DNA with said primer whose said template positioning segment contains a nucleotide mismatched with its adjacent nucleotide in the primer binding site of the double stranded DNA so that the identity of the adjacent nucleotide is changed in said amplicon by oligonucleotide-directed mutagenesis using said primer.

* * * * *